United States Patent [19]

Tran Dinh

[11] Patent Number: 4,836,069
[45] Date of Patent: Jun. 6, 1989

[54] PROCESS AND MEANS FOR CUTTING HARD OBJECTS OR MATERIALS WITHOUT CUTTING SOFTER OBJECTS OR MATERIALS

[76] Inventor: Can Tran Dinh, 23, avenue Neil, 75017 Paris, France

[21] Appl. No.: 87,289

[22] Filed: Aug. 20, 1987

[30] Foreign Application Priority Data

Aug. 20, 1986 [FR] France ............................ 86 11886

[51] Int. Cl.⁴ ............................................ A61F 15/02
[52] U.S. Cl. ......................................... 83/13; 30/388; 30/392; 128/317
[58] Field of Search ................ 30/392, 393, 394, 388; 128/317; 74/52; 83/13

[56] References Cited

U.S. PATENT DOCUMENTS

| | | | |
|---|---|---|---|
| 1,763,730 | 6/1930 | Von Lackum | 30/388 |
| 2,639,737 | 5/1953 | Forsberg | 30/392 |
| 3,103,069 | 9/1963 | Gary | 30/392 |
| 3,905,105 | 9/1975 | Tuke | 128/317 |
| 3,978,862 | 9/1976 | Morrison | |
| 4,018,090 | 4/1977 | Brems | 74/52 |
| 4,628,605 | 12/1986 | Clowers | 30/393 |

FOREIGN PATENT DOCUMENTS

| | | | |
|---|---|---|---|
| 0158325 | 10/1985 | European Pat. Off. | 30/392 |
| 1931890 | 1/1971 | Fed. Rep. of Germany | |
| 2430064 | 1/1976 | Fed. Rep. of Germany | |
| 3408189 | 9/1984 | Fed. Rep. of Germany | |

OTHER PUBLICATIONS

Machine Design, vol. 35, No. 30, Dec. 1963.

*Primary Examiner*—Frank T. Yost
*Assistant Examiner*—Scott A. Smith
*Attorney, Agent, or Firm*—Pollock, VandeSande & Priddy

[57] ABSTRACT

The invention concerns a process and apparatus for cutting hard objects or materials without cutting softer objects or materials.

In the invention, a transmission imparts to the cutting element a relatively slow periodic motion that is combined with a second, more rapid periodic motion consisting of relatively low-amplitude vibrations, with the second motion being imparted by oscillation. The invention may be applied to jigsaws and circular saws.

6 Claims, 2 Drawing Sheets

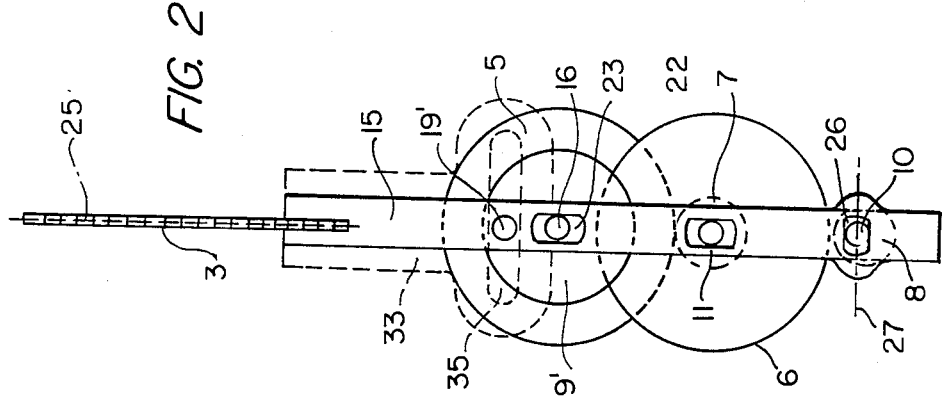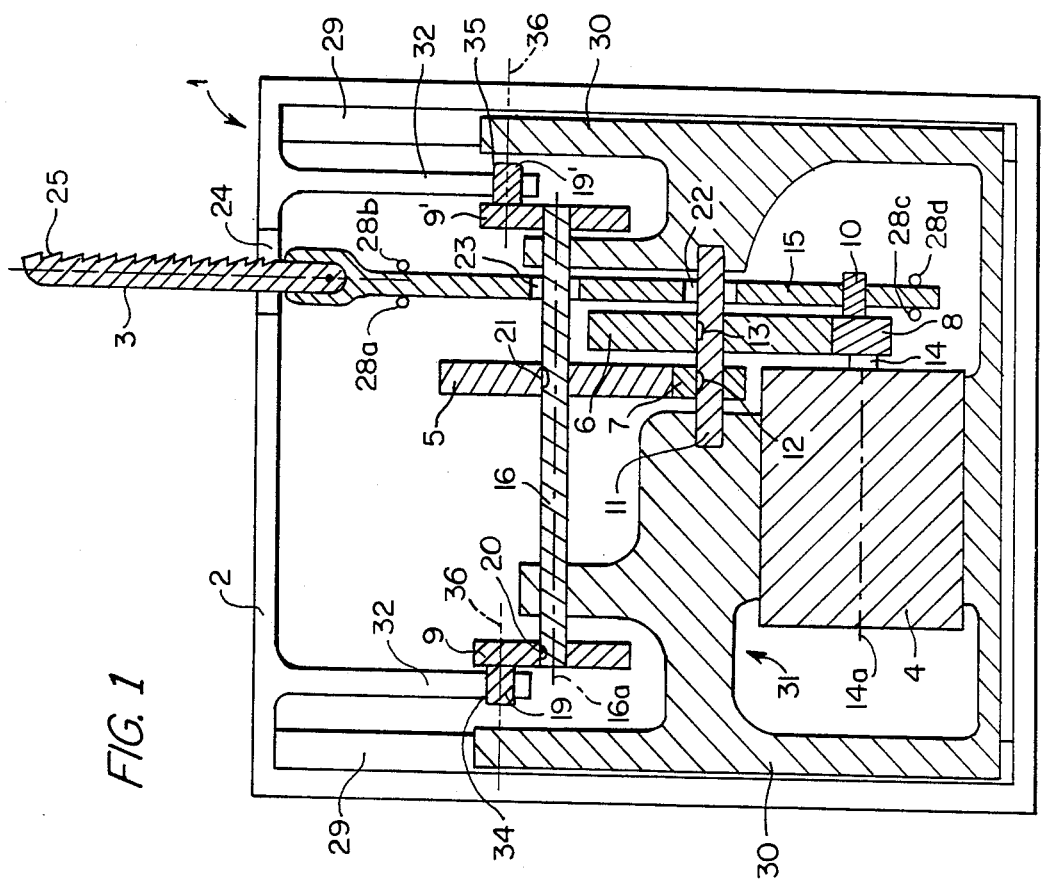

PROCESS AND MEANS FOR CUTTING HARD OBJECTS OR MATERIALS WITHOUT CUTTING SOFTER OBJECTS OR MATERIALS

TECHNICAL FIELD

The invention concerns a process and means for cutting hard objects or materials without cutting softer objects or materials.

BACKGROUND OF THE INVENTION

The prior art describes cutting means such as saws to which a periodic motion is imparted, generally by an electric motor, thus enabling such means to cut or convert various types of materials or objects.

Particular examples of this type of machine are circular saws and jigsaws, in which the cutting element consists respectively of a toothed disk driven in rotation about a stationary axis, or of a toothed blade driven in an alternating linear motion.

However useful such equipment may be, it has a number of drawbacks, notably that of cutting any material that is applied to or pushed against the cutting element, regardless of the hardness or softness of that material. In other words, if the user of such equipment is clumsy or inattentive, even for a few seconds, he runs the risk of seriously injuring himself if the cutting element comes into contact with a part of his body.

The process and means of the invention eliminate or at least considerably reduce such risks by effectively cutting hard materials or objects without cutting or damaging softer materials or objects such as human flesh.

SUMMARY OF THE INVENTION

For this purpose, the process of the invention requires that two combined motions be imparted to the cutting element. One motion has a relatively long period and is oriented in a certain direction of cut. The second motion, in the same cutting direction, is an oscillating motion with a smaller period than that of the first motion. In this way, the risks and dangers associated with the use of cutting mechanisms are considerably reduced. Furthermore, the lifetime of the machine is prolonged by the fact that the cutting element undergoes uniform wear and is not subject to overheating.

One embodiment of the invention provides more specifically that a relatively slow, alternating, linear movement of high amplitude is communicated to the cutting element along a given cutting axis, while, along the same cutting axis, a more rapid vibrating motion of lower amplitude is communicated to the cutting element as the latter occupies a series of positions in the course of its alternating, linear motion.

An equally attractive embodiment provides that a relatively slow movement of rotation about a fixed axis is communicated to the cutting element, while a more rapid vibrating movement of relatively smaller amplitude is imparted to the cutting element in the same cutting direction as the cutting element revolves through a series of successive positions.

It should be noted that, regardless of the embodiment used, the movements to which the cutting element is subjected are less violent and abrupt than with known circular or linear drive mechanisms, with the result that the cutting element receives less wear, thus facilitating its maintenance and extending its useful life.

Because the process of the invention is particularly applicable to jigsaws and circular saws, the means of the invention naturally comprise, in addition to a cutting element such as a saw blade, specific drive means applied to one or the other of these two types of saw.

The result is a cutting mechanism that is both effective and safe, whereas with known means of this type, in which a relatively rapid periodic movement of greater or lesser amplitude is imparted to the blade, the resulting cut is either dangerous or ineffective for hard materials such as wood.

BRIEF DESCRIPTION OF THE FIGURES

The process and means of the invention will be more clearly apparent from the following description, made with reference to the accompanying drawings, in which:

FIG. 1 is a schematic interior elevational view of one embodiment of the invention.

FIG. 2 illustrates in greater detail the gears and connecting parts of the means depicted in FIG. 1.

DETAILED DESCRIPTION OF THE INVENTION

Figure 3:
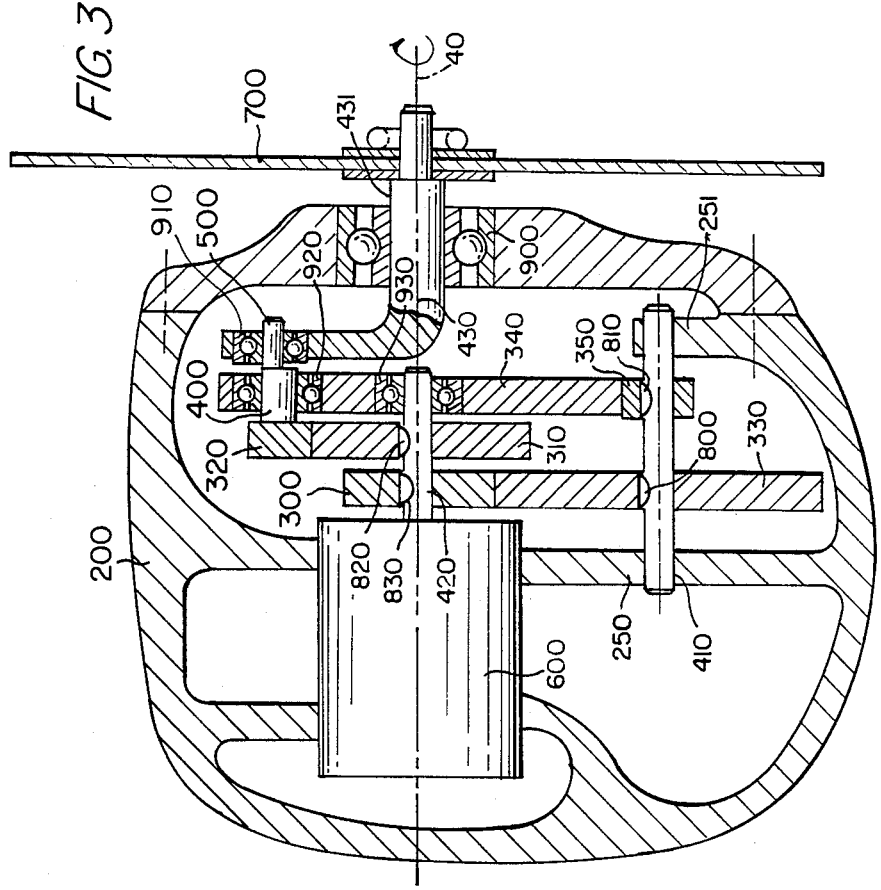
FIG. 3 is a schematic interior elevational view of a variant of the invention.

FIGS. 1 and 2 illustrate cutting means of the jigsaw type produced in accordance with the invention.

The means shown, designated overall by the numeral 1, comprise a body or housing 2 within which are positioned a support frame 31 capable of moving in translation with respect to housing 2, essentially along the axis 25 of a toothed blade 3, and drive and connection means required to impart to said blade periodic motions of different periods by means of a motor 4, preferentially electric, fastened to frame 31.

In the interest of clarity, all of the means making up the mechanism of the invention will be described.

Motor 4 drives in rotation an output shaft 14 that passes through a gear 8 to which it is attached. The end of said shaft 14 opposite the motor is extended in the form of a stub 10 mounted slightly off-center with respect to the axis of rotation 14a of shaft 14, onto which it is fastened. Stub 10 passes through a rod 15 that is integral with the blade. The passage is provided by an opening 26 that is elongated on an axis 27 that is essentially perpendicular to axis 25 of the blade and to shaft 14.

It will be understood that blade 3 constitutes the cutting element of the mechanism. Rod 15 extends along the axis of said blade into the body of the mechanism.

FIGS. 1 and 2 both show that gear 8 meshes with a gear 6 that transmits movement to a gear 7 through a shaft 11 and keys 12, 13.

Said shaft 11 is set into frame 31 at either end, and passes through gears 6 and 7 and rod 15 (through an opening 22 that is elongated in a direction essentially parallel to the direction of axis 25 of the blade). Shaft 11 is parallel to shaft 14 and is stationary in translation but free to rotate.

It will be noted that gear 7 meshes with another gear 5 which is itself connected on either side to two gears 9, 9' by means of a shaft 16 and two keys 20, 21.

Shaft 16 extends between gears 9, 9' in a direction parallel to shafts 11 and 14. In addition to gear 5, shaft 16 traverses rod 15 through an opening 23 that is elongated in a direction that is essentially parallel to the direction of axis 25 of the blade.

Gears 9, 9' are each provided with an eccentric stub 19, 19' that extends parallel to axis 16a of shaft 16. In order to guide the eccentric motion produced, each stub passes through a stationary part 32, 33 of housing 2, making use of openings 34, 35, which are elongated in a direction essentially parallel to axis 27 discussed above.

It will be noted that stubs 19 and 19' are mounted further off-center with respect to shaft 16 than is stub 10 with respect to motor output shaft 14.

Now that the principal means for driving the blade have been described, it will be noted that in FIG. 1 the movable part of the mechanism, supported by frame 31, has been marked with cross-hatches. Eccentric stubs 19, 19' provide the connection between stationary housing 2 and the set of means that make up the movable portion. They do this by being stationary in translation but free to rotate within parts 32 and 33 of said housing. In order to guide said mobile portion in its displacements parallel to axis 25, pairs of slides 29, 30 are provided on frame 31 and housing 2. In addition, rollers 28a, 28b, 28c, 28d, or equivalent means, may advantageously guide the rod 15 that drives the blade, which protrudes from housing 2 through an opening 24.

Figure 4:
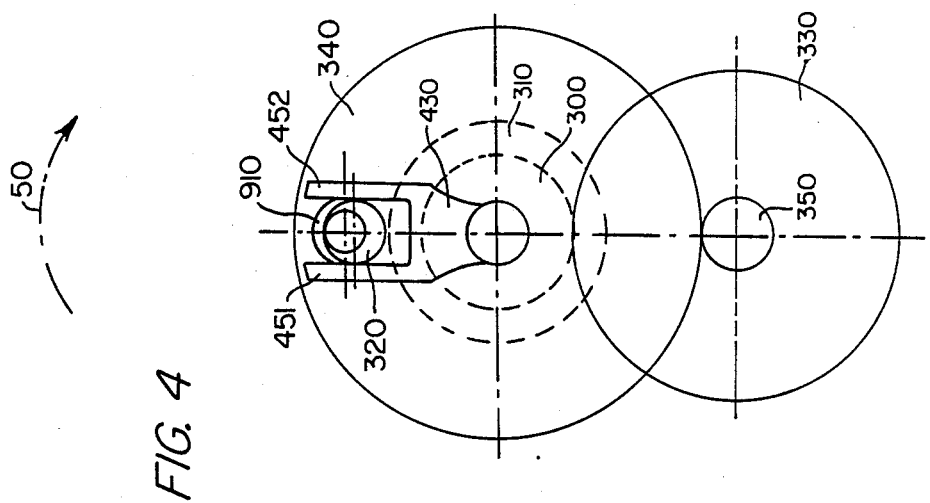
FIG. 4 more specifically illustrates the position of the various gears and the drive shaft of the means illustrated in FIG. 3.

FIGS. 3 and 4 illustrate a variant of the means of the invention in the form of a circular saw.

As with the first embodiment, only a portion of the means for driving and controlling the blade is covered by the invention. However, in the interest of clarity, all of the means contributing to the operation of said circular saw will be described in detail.

Like the mechanism illustrated in FIGS. 1 and 2, these means include a housing 200; various gear 300, 310–350; connecting shafts 400, 410 . . . 430; keys 800, 810, . . . 830; an electric motor providing rotational power; and a cutting element 700 in the form of a toothed disk.

This mechanism is further provided with ball bearings 900, 910 . . . 930 mounted on the shafts or on eccentric stub 500.

FIGS. 3 and 4 show clearly that motor 600, which is mounted so as to be stationary within housing 200, imparts rotational motion to an output shaft 420, which transmits said rotational motion to two gears 300 and 310. Each of the latter is locked onto the shaft with a key 830, 820.

Gear 300 meshes with another gear 330, while wheel 310 meshes with gear 320. Onto the latter gear is mounted a shaft 400 which extends parallel to shaft 420. Eccentric stub 500 is locked onto shaft 400. Said eccentric stub 500 extends into a ball bearing 910 mounted on an L-shaped shaft 430 that extends beyond housing 200 along an axis 40 that is parallel (or coextensive) with that of shaft 420. Shaft 430 is further protected by another ball bearing 900 mounted within the wall of said housing.

The protruding end 431 of shaft 430 imparts rotational motion to cutting disk 700.

Returning now to the gearing, it will be noted that gear 330, which is already connected to gear 300, transmits rotational motion to a gear wheel 350 by means of a shaft 410, parallel to shaft 420, and of keys 800 and 810, mounted on gears 330 and 350 respectively. Shaft 410, which is free to rotate, is set at either end into stationary sections 250, 251 of housing 200.

FIG. 3 in particular shows that gear 350 meshes with another gear 340, traversed by shafts 400 and 420, which were discussed above. Said shafts pass through ball bearings mounted on said gear 340 and designated 920 and 930 respectively.

Referring now to FIG. 4, it can been that shaft 430, which drives the cutting disk, is forked at the point at which it meets eccentric stub 500. The two prongs 451, 452 of the fork contain ball bearing 910, into which extends eccentric stub 500.

With two examples of variants of the means of the invention having been described, the functioning of those examples will now be discussed. In the examples, two periodic motions occurring in a single cutting direction but having different periods are combined and communicated to a cutting element (or possibly other equivalent means) designed to cut hard objects or materials without cutting or damaging softer objects or materials.

More specifically, the parts making up the jigsaw illustrated in FIGS. 1 and 2 act in such a way that it is possible to communicate to blade 3, in the cutting direction shown by axis 25, a relatively slow, alternating linear movement of high amplitude and a more rapid vibrational motion of low amplitude. The latter movement is produced in a series of positions occupied by the blade in the course of its alternating linear motion.

The two movements are combined as follows.

(a) Osillatory or vibratory motion of the saw blade.

Eccentric stub 10 is locked onto shaft 14, which in turn is controlled by motor 4. Said stub 10 drives rod 15, and therefore blade 3, in a rapid, longitudinal reciprocal motion of low amplitude. Said motion occurs essentially within axis 25. It will be noted that, for this purpose, rod 15 is guided by two shafts 11 and 16, which pass through elongated openings 22 and 23, and by rollers 28a, 28b, 28c, and 28d.

(b) Reciprocal motion of the blade and of the entire movable portion of the mechanism.

Through a system of reduction gears 8–6, 7–5, wheels 9, 9', each carrying an eccentric stub 19, 19', revolve slowly about the common axis 36 of the stubs, thereby communicating a relatively slow and broad reciprocal motion along axis 25 to the entire movable portion of the mechanism, and particularly blade 3.

With reference to the circular saw variant of the invention, it will be noted that instead of imparting an alternating linear motion to the cutting element, the means of the invention communicate to the latter, in the cutting direction shown by arrow 50, a relatively slow rotational movement about a stationary axis 40, combined with a more rapid vibratory motion of relatively low amplitude and occurring in the same cutting direction. Said vibratory motion is produced as the cutting element, i.e., toothed disk 700, occupies a series of positions in the course of its rotational motion.

The two combined movements are produced as follows.

(a) Oscillatory or vibratory motion of disk.

Gear 310, driven by shaft 420 and motor 600, produces higher revolutions in gear 320, which carries shaft 400 and its eccentric stub 500. Surrounding the latter is a ball bearing 910. Said stub 500 imparts to L-shaped shaft 430 a relatively rapid oscillatory motion about main axis 40. Said motion is transmitted by shaft 430 to the teeth of disk 700.

(b) Rotation of disk.

Gear 300 is also connected to shaft 420 and driven by motor 600. Through reduction gears 330, 350, and 340, said gear 300 drives shaft 430 in a rotational motion that is relatively slow with respect to the foregoing vibratory motion.

Disk 700 is therefore driven about fixed axis 40 in a combined movement of relatively slow rotation and much more rapid oscillation, with both movements occurring in a single cutting direction 50.

The invention is naturally not limited to the embodiments that have been described in detail. Rather, it embraces all possible variants that might include equivalent means.

In particular, a cam system, vibrator, or electropneumatic system might complement or replace the eccentric stub in producing the vibratory or oscillatory movement of the cutting element.

I claim:

1. A process for cutting material with a saw blade having cutting teeth by placing the teeth of said blade against said material in cutting contact therewith while simultaneously moving said blade in first and second periodic motions, said first motion having a relatively long period and high amplitude and said second motion having a relatively short period and low amplitude, and causing the teeth of said blade to move along the same line in said second motion as it is moved along in said first motion, whereby relatively hard materials may be cut without cutting relatively soft materials when both hard and soft materials are in contact with said blade.

2. A process according to claim 1 wherein said first motion comprises moving said blade in a relatively slow back and forth linear motion having a relatively high amplitude and said second motion comprises moving said blade in a relatively fast back and forth linear motion at a relatively low amplitude.

3. A process according to claim 1 wherein said first motion comprises moving said blade in a relatively slow rotational motion about an axis and said second motion comprises a relatively rapid circular oscillatory movement about said axis, said oscillating movement having a low amplitude.

4. Cutting means of the jigsaw type, characterized in that said means comprise:
    a housing comprising a stationary portion and a moving portion,
    a cutting blade that extends into the frame in the form of a control rod mounted so as to move in translation with respect to the stationary portion of the frame through drive means connected to said moving portion, with said drive means comprising
    a motor that produces revolutions in a shaft,
    a series of gears enmeshed with said shaft (14) and forming means for the transmission of said rotational motion to a second shaft onto which is fastened at least one eccentric providing a connection to the stationary portion of the frame, with respect to which said at least one eccentric is mounted so as to be free to rotate, with said second shaft being mechanically connected to said rod in such a way as to drive it in relatively slow and alternating axial movements of relatively high amplitude along an axis, and
    a second eccentric, fastened to said first shaft and connected mechanically to said rod in such a way as to drive it, in the course of its alternating, axial, linear motion, in a second, oscillating motion taking place along said axis.

5. Cutting means of the circular saw type, characterized in that said means comprise:
    a housing,
    a cutting blade located outside the housing and mounted so as to be able to move with respect to the latter along a certain cutting line by the action of drive means comprising:
    a motor that produces revolutions in a first shaft,
    a series of gears enmeshed with said first shaft and forming means for the transmission of rotational motion to a second shaft,
    a third shaft (430), mechanically connected on one end to said second shaft wherein a portion of said third shaft projects from the housing to the blade, so that said blade is driven in rotation about an axis (40) along said cutting line, and
    an eccentric, fastened to said second shaft and forming a means of mechanical connection between said second shaft and said third shaft, with respect to which said eccentric is free to rotate, so that said blade, in the course of the rotational motion of said eccentric, will be driven in an oscillating motion along said cutting line.

6. Cutting means of claim 5, characterized in that said third shaft, at its connection with the eccentric, takes the shape of a fork comprising two prongs of which said eccentric is free to revolve.

* * * * *